United States Patent [19]

Jayne et al.

[11] 4,093,554

[45] June 6, 1978

[54] HYDRAULIC FLUID COMPOSITIONS

[75] Inventors: Gerald John Joseph Jayne; Herbert Frank Askew; Colin John Harrington, all of Wokingham, England

[73] Assignee: Castrol Limited, Swindon, England

[21] Appl. No.: 562,253

[22] Filed: Mar. 26, 1975

[30] Foreign Application Priority Data

Mar. 27, 1974 United Kingdom ............... 13708/74

[51] Int. Cl.² .......................... C09K 50/00; C07F 7/18
[52] U.S. Cl. ............................. 252/78.3; 260/448.8 R
[58] Field of Search ..................... 252/78; 260/448.8 R

[56] References Cited

U.S. PATENT DOCUMENTS

| | | | |
|---|---|---|---|
| 2,559,342 | 7/1951 | Burkhard | 260/448.8 R |
| 2,916,461 | 12/1959 | Krantz | 260/448.8 R X |
| 3,029,269 | 4/1962 | Abbott et al. | 260/448.8 R |
| 3,336,227 | 8/1967 | Göthel et al. | 260/448.8 R X |
| 3,383,315 | 5/1968 | Göthel et al. | 260/448.8 R X |
| 3,444,081 | 5/1969 | Göthel et al. | 260/448.8 R X |
| 3,514,402 | 5/1970 | Göthel et al. | 260/448.8 R X |
| 3,994,948 | 11/1976 | Jayne et al. | 260/448.8 R |

Primary Examiner—Paul F. Shaver
Attorney, Agent, or Firm—Bacon & Thomas

[57] ABSTRACT

Novel compounds useful in hydraulic fluid compositions as additives, as base stock or as members of a blended base stock are glycol-substituted aryl silanes of the formula:

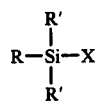

wherein:
(a) R is aryl;
(b) X is selected from the group consisting of

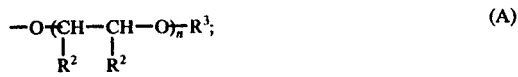

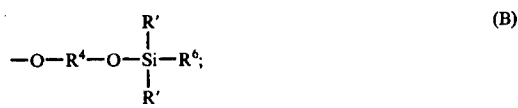

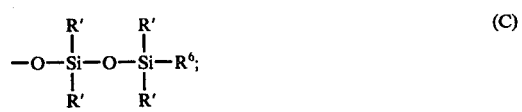

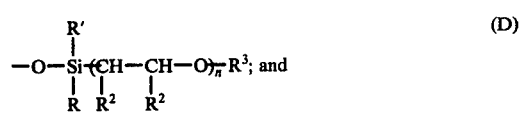

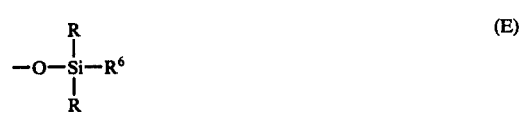

in which each $R_2$ is defined above, R' is as hereinafter defined, each $R^2$ is independently selected from the group consisting of hydrogen, methyl and ethyl, $R^3$ is alkyl, $R^4$ is selected from the group consisting of diol and polyol residues, $R^6$ is selected from the group consisting of aryl and alkyl, and $n$ is an integer; and (c) each R' is, independently selected from the group consisting of groups of formula (A) as defined above, alkyl, aryl, and groups of the formula:

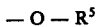

wherein $R^5$ is alkyl and if the glycol-substituted aryl silane contains more than one group $R^5$ they may be the same or different; provided that the glycol-substituted arylsilane contains at least one group selected from the group consisting of

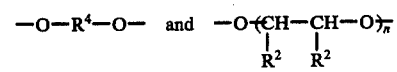

wherein $R^2$, $R^4$ and $n$ are as defined above.

The new silanes may be made from chlorosilanes by various condensation methods or by transesterification procedures.

44 Claims, No Drawings

HYDRAULIC FLUID COMPOSITIONS

This invention relates to hydraulic fluid compositions, more particularly to hydraulic fluids having high boiling point and vapour lock temperatures.

Hydraulic fluids based on glycol ethers have been used in, for example, vehicle brake and clutch systems for many years and still remain the most commonly used type of fluid. However, specifications of required quality standards laid down by hydraulic systems manufacturers and non-commercial organisations such as the Society of Automotive Engineers have become progressively more severe. In particular, a need has arisen for fluids having higher boiling points and, more importantly, higher vapour lock temperatures both for the fluid as formulated by the manufacturers and also for the fluid in the presence of water. Glycol ether based fluids are known to be deficient in this respect due to the hygroscopicity of the fluid which results in the absorption of water from the atmosphere. This in turn reduces the boiling point and vapour lock temperature of the fluid and with extended use the water content of the fluid can build up to a level at which the boiling point and vapour lock temperatures are reduced to a dangerous extent. When subjected to heat, e.g. generated by heavy braking, the fluid may boil or vaporise to a sufficient extent to cause a serious brake malfunction.

Hydraulic fluids having low hygroscopicity have been developed, based on glycol esters, to deal with this problem. Such fluids are relatively insensitive to the effect of atmospheric moisture, but are more expensive than glycol ether based fluids and have certain technical disadvantages, e.g. their viscosity properties are inferior to those of glycol ether based fluids. Consequently, use of these low hygroscopicity fluids has been mainly limited to where the desirable properties such as high boiling point and vapour lock temperatures are deemed to outweigh their disadvantages. Other types of water insensitive fluids have also been developed. Nevertheless, manufacturers are still seeking new fluids which combine as many as possible of the desirable properties of both glycol ether based and low hygroscopicity fluids and, desirably, have even higher boiling points and/or vapour lock temperatures than the low hygroscopicity fluids.

Recently, there has emerged a growing tendency in vehicle design to use a single hydraulic system to operate equipment, such as power-steering, shock absorbers and brakes, which hitherto were provided with separate hydraulic systems. This has created serious problems in the formulation of suitable fluids. The mineral oil based fluids hitherto used in power-steering systems and shock absorbers are satisfactory with respect to the nitrile and chloroprene rubber used for the seals and gaskets in such systems but are highly detrimental to the natural and synthetic rubbers used in the construction of hydraulic brake and clutch systems. This results in excessive swelling of the latter seals which can lead to a serious malfunction of the brake or clutch system. Conversely, the fluids hitherto used in brake and clutch systems, which are normally based on glycols, glycol ethers and/or glycol ether esters, and which have operated satisfactorily in such systems, have a detrimental effect on the nitrile and chloroprene rubber gaskets used in power-steering systems and shock absorbers which can also lead to malfunctioning. In the case of vehicle operation the characteristic of reliability in operation, which is generally desirable in all mechanical devices, is increased in importance to an absolutely essential requirement by virtue of safety considerations. The need has therefore arisen for a fluid which can be used satisfactorily in a central system controlling the operation of a number of different items of equipment.

We have now found certain silicon compounds which combine good viscosity characteristics and excellent vapour lock temperatures which are relatively insensitive to the effect of atmospheric moisture. By virtue of these properties the compounds are useful in the formulation of improved hydraulic fluids. Moreover, this combination of desirable properties provides an opportunity for blending with known hydraulic fluid base stocks which may provide blends suitable for uses, such as in central hydraulic systems for which hitherto it had been extremely difficult, or even impossible to provide fully satisfactory fluids.

Accordingly, the present invention provides a glycol-substituted aryl silane of the formula:

wherein:
(a) R is an aryl; preferably phenyl or substituted phenyl group wherein the substituents are preferably short chain alkyl groups.
(b) wherein X is a group of the formula:

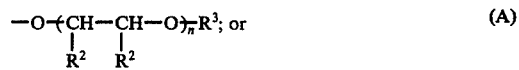  (A)

  (B)

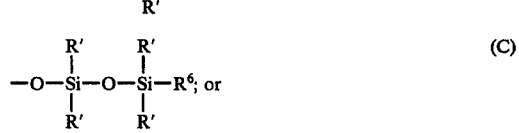  (C)

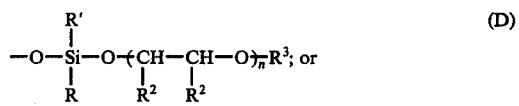  (D)

  (E)

(c) each $R^6$ is as R or an alkyl group and each group $R^6$ may be the same as or different from any other group $R^6$;
(d) each R' is as $R^6$ or R or is a group of the formula:

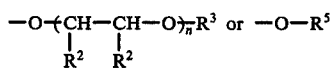

and each R' may be the same or different from any other group R';
(e) each $R^2$ is a hydrogen atom or a methyl or ethyl group and each $R^2$ may be the same as or different from any other group $R^2$ provided that when any group $R^2$ is methyl or ethyl the group $R^2$ on the immediately adjacent carbon atom is hydrogen;

(f) each $R^3$ is an alkyl group and each group $R^3$ may be the same as or different from any other group $R^3$;

(g) $R^4$ is the residue of a diol or polyol;

(h) each $R^5$ is an alkyl group, preferably containing 1 to 6 carbon atoms and each $R^5$ may be the same as or different from any other group $R^5$;

(i) each $n$ is an integer, preferably from 1 to 10, more preferably 1 to 6, especially 1 to 4;

(j) provided that the glycol-substituted aryl silane contains at least one group of the formula:

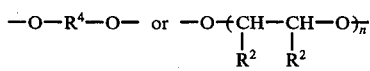

In the case of glycol-substituted aryl silanes for use in hydraulic brake and clutch systems it is preferable for groups $R^6$, $R^3$ and $R^5$ to be relatively short chain alkyl groups, e.g. containing from 1 to 4, more preferably 1 or 2, carbon atoms, in order to minimise the rubber swelling effect on the seals and gaskets used in such systems. However when used in a central system it may be more desirable to effect a compromise between the requirements, often conflicting, for each of the various seal and gasket materials. In this case some, or all, of the groups $R^6$, $R^3$ and $R^5$ may be longer chain alkyl groups, e.g. up to 6, or even 8, carbon atoms.

Preferred compounds are when R is phenyl, one R' is methyl, the other R' and X are the same and have the formula:

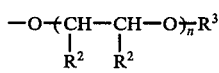

particularly preferred compounds have the formula:

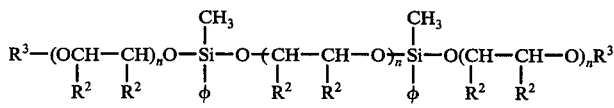

wherein $R^2$, and $R^3$ have the same significance as above and n is from 1 to 4.

The glycol-substituted aryl silane hydraulic fluid components of the present invention may be readily prepared from aryl chlorosilanes by reaction with glycols, other diols, polyols, glycol monoalkyl ethers or alkanols as appropriate using well known techniques. Thus in the case where X is a group of formula (A) preparation may be by reaction of an aryl chlorosilane with an ethylene glycol monoether of the formula:

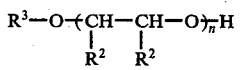

in which each $R^2$ is a hydrogen atom. Compounds in which both R' are as R may be prepared from triaryl chlorosilanes. Similarly compounds in which one R' is as R and the other R' is a further glycol monoether residue or compounds in which both groups R' are further glycol monoether residues can be prepared from diaryl dichlorosilanes and aryl trichlorosilanes respectively. Analogous compounds may be prepared in the same way from propylene and butylene glycol monoethers. Alternatively mixed glycol monoethers may be used, e.g. glycol monoethers containing a mixture of ethylene and propylene residues. The aryl chlorosilane may be reacted with the glycol monoether in stoichiometric proportions or an excess of the latter reactant may be used. To ensure substantially complete conversion it is preferred to use an excess of glycol monoether, but normally only a slight excess, e.g. about 10%, is required for this purpose. If desired compounds containing 2 or 3 different glycol monoether residues may also be prepared by reacting diaryl dichlorosilanes or aryl trichlorosilanes with 2 or 3 different glycol monoethers. This may be carried out by reaction with a mixture of glycol monoethers in a single stage reaction. However, a more preferred technique is to react the aryl chlorosilane sequentially with each glycol monoether. In this case careful control of the proportions of reactants used is very desirable. A useful technique is to use a slight excess, e.g. 10%, of glycol monoether in each stage to allow for incomplete reaction. Similar provisions will apply when starting from an alkyl aryl dichlorosilanes.

In compounds prepared in this manner all groups R' will be glycol monoether groups of the formula:

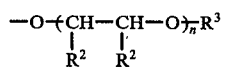

or a R. Compounds in which one or more groups R' have the formula —O—$R^5$ may be prepared in the same manner using a glycol monoether and an alkanol of formula H—O—$R^5$. In this case also reaction may be a single stage operation, using a mixture of glycol monoether and alkanol, or may be carried out sequentially.

Compounds wherein X has the formula (B) may be prepared by reaction of the appropriate monochlorosilane with a diol or polyol. Thus reaction of triaryl chlorosilane with a glycol of formula

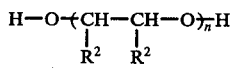

produces a compound of formula

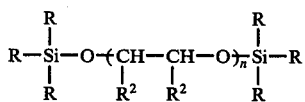

Alternatively a diaryl or alkyl aryl dichlorosilane or aryl trichlorosilane may be reacted with 1 or 2 moles respectively of glycol monoether to produce a diaryl or alkylaryl glycol monoether chlorosilane or an aryl-di(glycol monoether) chlorosilane which is then reacted with glycols simultaneously in a single stage reaction. Such a single stage reaction may be more convenient but is more difficult to control and therefore sequential reaction is preferred.

In place of the glycol a polyol may be used such as trimethylol propane, pentaerythritol or dipentaerythritol to produce compounds in which two silicon atoms are linked through the group —O—$R^4$—O—, which is the residue of the polyol. In this case R⁴ may bear one or more residual hydroxy groups. Alternatively, sufficient chlorosilane may be used to react with more than two hydroxy groups of the polyol so that groups

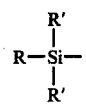

are introduced in place of residual hydroxy groups.

Preferred compounds in which X has the formula (B) are those in which each silicon atom bears at least one glycol monoether residue and most preferably each silicon atom bears two glycol monoether residues.

In compounds wherein X has the formula (B) prepared in the above described manner all groups R' will be as R or glycol monoether groups. Compounds in which one or more groups R' have the formula —O—R⁵ may be prepared in the same manner by using an alkanol of formula H—O—R⁵ in place of at least a part of the glycol monoether.

Compounds in which X has the formula (C), (D) or (E) contain an Si—O—Si linkage and may be prepared from suitable precursors using known techniques. Thus a diaryl or alkylaryl glycol monoether chlorosilane or an aryl di-(glycol monoether) chlorosilane may be hydrolysed to form a disiloxane (X = formula (D)) of formula:

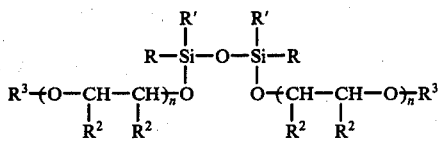

In yet another alternative, compounds of the formula:

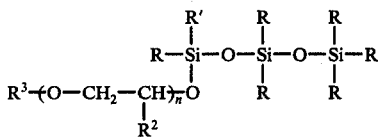

may be prepared from a triaryl chlorosilane, a diaryl dichlorosilane or an aryl di-(glycol monoether) chlorosilane.

In the preparation of the compounds of the present invention which may be used as hydraulic fluid components, the reaction of a chlorosilane with a hydroxyl group (to introduce either one or more glycl monoether residues or the group —O—R⁴—O— or one or more groups —O—R⁵ into the molecule) may be carried out in the presence of an acid acceptor or inert gas purge to remove liberated hydrogen chloride. Especially preferred acid acceptors are tertiary bases such as pyridine.

An alternative method of preparing compounds in accordance with the present invention is by transesterifying a —Si—O—R group wherein R is a lower alkyl preferably methyl or ethyl group, with a suitable alcohol, glycol, glycol ether or poly oxyalkylene glycol ether preferably in the presence of a suitable catalyst.

The invention also includes a hydraulic fluid composition comprising a glycol-substituted aryl silane as defined above.

The glycol-substituted aryl silane hydraulic fluid components may be used as an additive, as a base stock or as a component of a blend of base stocks. The proportions employed may therefore vary over a very wide range. When used as a base stock the glycol-substituted aryl silanes will constitute the bulk of the hydraulic fluid, for example from 75% or 80% to 99% by weight, based on the total weight of the hydraulic fluid. The remainder of the hydraulic fluid may be composed of conventional hydraulic fluid additives, as more fully described hereinafter, and/or small quantities of other hydraulic fluid base-stocks, as also more fully described hereinafter.

When used as a component of a blend of base stocks the total blend of base stocks will likewise constitute the bulk of the hydraulic fluid. In this case, the base stocks may be predominantly one or more glycol-substituted aryl silanes blended with a lesser quantity of one or more other base stocks, of the type hereinafter described, so as to modify the proportion of the glycol-substituted alkyl silanes. Thus the hydraulic fluid may contain, for example 55% to 70% by weight of one or more glycol-substituted aryl silanes based on the total weight of the hydraulic fluid. Alternatively, one or more other base stocks may be modified by blending with a lesser quantity of glycol-substituted aryl silanes so that the hydraulic fluid contains, e.g. from 20% to 40% by weight glycol-substituted aryl silane. In addition, a compromise between the properties of the glycol-substituted aryl silanes and the other fluids may be effected by blending in approximately equal quantities to provide fluids containing from 40% to 55% glycol-substituted aryl silane.

When used as an additive, the glycol-substituted aryl silanes are principally useful in suppressing the sensitivity of hydraulic fluids, and in particular, the boiling point and vapour lock temperatures of the fluids, to water. In this role, the glycol-substituted silanes may be used in an amount of e.g. from 0.5% up to 15% or 20%, more preferably 1 to 12%, by weight based on the total weight of the hydraulic fluids. The bulk of such fluids will be constituted by one or more base stocks as hereinafter described.

When the glycol-substituted aryl silanes are used as a component of a blend of base stocks the resulting hydraulic fluids may contain conventional hydraulic fluid additives in like manner as when the base stock substantially consists of the glycol-substituted aryl silanes. Similarly, when used as an additive the glycol-substituted alkyl silanes may, if desired, be used in conjunction with conventional hydraulic fluid additives.

Base stock with which the glycol-substituted alkyl silanes may be blended, or with which they may be used as additives include glycol ethers, glycol esters, glycol orthoesters and borate esters. Glycol ether base stocks are well known and suitable examples thereof are those commonly used in hydraulic fluids. The preferred glycol ester base stocks are those having the general formula:

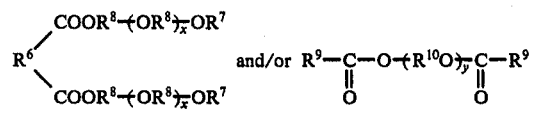

I  II wherein $R^6$ is a straight or branched chain alkylene group containing at least 2, preferably 2 to 8, carbon atoms, each $R^7$ is the same or different and is an alkyl radical containing from 1 to 4 carbon atoms or a phenyl radical, each $R^8$ is the same or different and is an ethylene, propylene or butylene group, each $x$ is the same or different and is 0 or an integer of from 1 to 3, each $R^9$ is the same or different and is an ethyl or methyl group, each $R^{10}$ is the same or different and is an ethylene or propylene group and $y$ is an integer, preferably an integer such that the total number of carbon atoms in the $-(R^{10}O-)_y$ group is from 4 to 12, more preferably 4 to 9.

The dicarboxylic acid esters of formula I are described in U.K. Patent No. 1,083,324. Esters which may suitably be used in the present invention are the succinates, glutarates, adipates, azelates, sebacates, isosebacates and nylonates of methyl, ethyl propyl and butyl oxitol, dioxitol and trioxitol described in Specification No. 1,083,324, the nylonates, especially di(methyl dioxitol) nylonates, being particularly preferred.

The glycol di-esters of formula II are known compounds and the preferred glycol di-esters are the glycol dipropionates described in U.K. Patent No. 1,249,803. It is preferred that the hydraulic fluids comprise not more than 50% by weight of the glycol di-esters; the remainder, if any, of the carboxylic acid ester component being the esters of formula I.

Numerous varieties of borate ester base stocks are known and these may be depicted by the following general formulae:

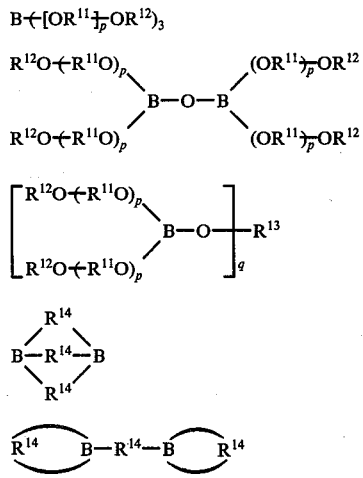

wherein each $R^{11}$ is the same or different and is a straight or branched chain alkyl group, each $R^{12}$ is the same or different and is an alkyl group, each $p$ is the same or different and is an integer, $q$ is an integer of from 2 to 6, $R^{13}$ is the residue of a di- or poly-hydroxy organic compound having a number of reactive hydroxy groups equal to $q$, and each $R^{14}$ is the same or different and is the residue of a di-hydroxy organic compound which residue is attached to each boron atom via an oxygen atom.

These borate esters are more fully described in our copending Application No. 2873/71 and Cognate Application No. 34240/71, (and corresponding published German Offenlegungsschrift No. P2202732) to which reference may be made for further details.

Further base stocks which may be used are the glycol orthoesters described in British Pat. Specification No. 1,330,468 having the general formula:

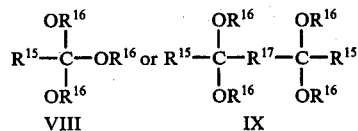

wherein $R^{15}$ is a hydrogen atom, and alkyl radical containing from 1 to 5 carbon atoms, or the same as $OR^{16}$; each $R^{16}$ is the same or different and each is an alkyl radical containing from 1 to 4 carbon atoms, an oxyalkylene glycol monoether radical, or a polyoxyalkylene glycol monoether radical containing from 2 to 20 alkylene oxy units, provided that at least one $R^{16}$ is an oxyalkylene glycol monoether radical or a polyoxyalkylene glycol monoether radical; and $R^{17}$ is an alkylene radical containing from 1 to 12 carbon atoms, provided that $R^{15}$ is then the same as $OR^{16}$ or $R^{17}$ is the group $-O-(R^{18}O)_z$, wherein each $R^{18}$ is the same or different and each is an alkylene radical containing from 2 to 8 carbon atoms and $z$ is an integer from 1 to 6. Reference may be made to the above mentioned British Pat. Specification No 1,330,468 for further details of such glycol orthoesters.

In a particular preferred embodiment of the present invention the glycol-substituted aryl silanes are used, either as an additive or as a component of a blend of base stocks, in hydraulic fluids comprising a mixture of glycol ethers and borate esters of foregoing formula III.

In another particularly preferred embodiment of the present invention the glycol-substituted alkyl silanes are used, either as an additive or as a component of a blend of base stocks, in hydraulic fluids comprising one or more glycol esters of foregoing formulae I and/or II or comprising a mixture of one or more glycol esters of foregoing formula I and/or II with one or more borate esters of foregoing formulae III to VII especially borate esters of formula III.

The hydraulic fluids of the present invention may also include minor proportions of polyoxyalkylene glycols or ethers thereof e.g. those sold by Union Carbide Corporation under the Registered Trade Mark "Ucon", particularly those of the LB and HB series. Suitable examples of these polyoxyalkylene glycols and their ethers and esters are given in British Pat. No. 1,055,641.

Typical additives which may be used in, or in conjunction with, the glycol-substituted alkyl silanes are lubricity additives selected from castor oil or castor oil treated in various ways, for example:

Firsts Castor Oil,

Castor oil to Specification DTD72

Blown castor oil, i.e. castor oil blown with air or oxygen while being heated.

Special Pale Blown Castor Oil, i.e. a similarly blown castor oil.

"Hydricin 4" i.e. a commercially available ethylene/oxide/propylene oxide treated castor oil.

Other lubricity additives which may be incorporated in hydraulic fluids in accordance with the present invention include borate esters e.g. tricresyl borate and borate ester condensates; and phosphorus-containing esters, especially phosphates e.g. tricresyl phosphate.

Other suitable lubricity agents are orthophosphate or sulphate salts of primary or secondary aliphatic amines having a total of from 4 to 24 carbon atoms, dialkyl citrates having an average of from 3½ to 13 carbon atoms in the alkyl groups, aliphatic dicarboxylic acids and esters thereof, specific examples being Diamylamine orthophosphate
Dinonylamine orthophosphate
Diamylamine sulphate
Dinonyl citrate
Di(2-ethyl hexyl) citrate
Polyoxyethylene sebacate derived from a polyoxyethylene glycol of M.W. 200
Polyoxyethylene azelate derived from a polyoxyethylene glycol of M.W. 200
Polyoxyethylene adipate derived from a polyoxyethylene glycol of M.W. 200
Polyoxyethylene/polyoxypropylene glutarate derived from mixed polyoxyglycols of average M.W. of about 200
Glutaric acid
Azelaic acid
Sebacic acid
Succinic acid
Di ethyl sebacate
Di 2-ethyl hexyl sebacate
Di iso octyl azelate Unsaturated aliphatic acids or their salts may also be used e.g. oleic acid or potassium ricinoleate.

Corrosion inhibitors which may be used in the present invention may be selected from heterocyclic nitrogen containing compounds, e.g. benzotriazole and benzotriazole derivatives such as those described in British Pat. Specification No. 1,061,904 or mercapto benzothiazole. Many amines or derivatives thereof are also suitable as corrosion inhibitors, for example di n-butylamine
di n-amylamine
cyclohexylamine
morpholine
triethanolamine and soluble salts thereof e.g. cyclohexylamine carbonate.

Phosphites are also good corrosion inhibitors e.g.
Tri phenyl phosphite
Di isopropyl phosphite and certain inorganic salts may be incorporated e.g. sodium nitrate.

Other additives which may be included are antioxidants such as diarylamines e.g. diphenylamine, p,p'-dioctyl-diphenylamine, phenyl-α-naphthylamine or phenyl-β-naphthylamine. Other suitable antioxidants are those commonly known as hindered phenols which are exemplified by 2,4-dimethyl-6-t-butyl phenol
2,6-di-t-butyl-4-methyl phenol
2,6-di-t-butyl phenol
1,1-bis (3,5-di-t-butyl-4-hydroxyphenyl)-methane
3,3',5,5'-tetra-t-butyl-4-4'-dihydroxydiphenyl
3-methyl-4,6-di-t-butyl phenol.
4-methyl-2-t-butyl phenol Yet further additives which may be used are phenothiazine and its derivatives, for example those having alkyl, or aryl, groups attached to the nitrogen atom or to the aryl groups of the molecule.

Other additives which may be used include alkylene oxide/ammonia condensation products as corrosion inhibitor, for example the propylene oxide/ammonia condensation product described in U.K. Pat. Specification No. 1,249,803. Further lubricity additives which may be used are complex esters, such as that sold under the trade name Reoplex 641 and also described in Specification No. 1,249,803. Moreover, long chain (e.g. $C_{10-18}$) primary amine corrosion inhibitors and polymerised quinoline resin antioxidants, as described in Specification No. 1,249,803, may be used, examples of such amines and resins being the commercially available materials Armeen 12D and Agerite resin D respectively.

Conventional additives such as those hereinbefore described are normally employed in small amounts such as 0.05% to 10%, for example, 0.1% to 2% by weight.

Regardless of precise composition it is highly desirable that the hydraulic fluids of the present invention have a kinematic viscosity at −40° C. of not more than 5,000 cSt, especially not more than 2,000 cSt. It is also desirable that the hydraulic fluids have a boiling point of at least 260° C.

The present invention is illustrated by the following examples.

EXAMPLE I

Toluene (2.5 liters) and phenyl trichlorosilane (211g 1 mole) were placed in a stirred glass vessel cooled by a water bath. Diethylene glycol mono methyl ether (396g 3.3 moles) and pyridine (261g 3.3 moles) were mixed and slowly added over 30 minutes whilst maintaining the temperature below 43° C. The mixture increased in viscosity and a granular white precipitate (pyridine hydrochloride) was formed. After heating to 100° C for 4 hours the mixture was allowed to cool, filtered and stripped to 100° C/20 Torr, followed by a further stripping to 188° C/0.1 Torr and then filtered through a filter aid pad. 363g (79%) of tris (methyl diglycol) phenyl silane was obtained, the structure of the product being provided by infra-red analysis and elemental analysis % Si = 6.38 (Calc 6.06) % Cl = 0.03 (Calc = zero).

EXAMPLES II and III (See later Table I).

EXAMPLE IV

Diethylene glycol bis (methyl diglycol methyl phenyl silane) was prepared in similar manner to that of Example I except that a mixture of diethylene glycol (159g 1.5) and pyridine (237g 3m) was added to methyl phenyl dichlorosilane (573g 3m) in toluene (2.5L). After the addition was complete the temperature was raised from below 50° C to 100° C. and maintained for 4 hours.

The reaction mixture was again cooled to below 50° C and a mixture of diethylene glycol mono methyl ether (396g 3.3m) and pyridine (260.7g 3.3m) added. When the exotherm had settled the temperature was again raised to 100° C for 4 hours and the product isolated as before. 561.4g (64%) of the product containing 10.8% Si (Calc 9.62) and less than 0.1% Cl (Calc zero)

The product has the formula:

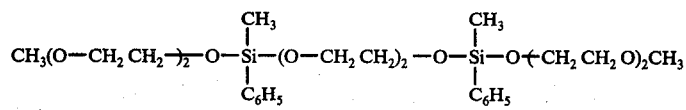

EXAMPLE V

Tris (methyl triglycol) phenyl silane was prepared by heating a mixture of triethylene glycol monomethyl glycol (656g 4 mole), phenyl triethoxy silane (240g 1 mole) and tetraisopropyl titanate (1ml) under a 12" packed and lagged column. 116.2g ethanol (Calc 138g) was removed from the head of the column. After stripping under vacuum and filtering 550.6g (92.5%) of a product containing 5.06% Si (Calc 4.73) was obtained.

Further preparations were carried out in substantially the same manner as in Example I or Example IV and the results of these preparations are given in Table I.

TABLE I

| Example No | Product Name | Silane | Wt(g) | mole |
|---|---|---|---|---|
| II | tris(methyl triglycol) phenyl silane | Ph Si Cl$_3$ | 211 | 1 |
| III | bis(methyl triglycol) methyl phenyl silane | Me Ph Si Cl$_2$ | 382 | 2 |
| VI | tris(methyl diglycol) phenyl silane | Ph Si Cl$_3$ | 359 | 1.7 |
| VII | tris(dipropylene glycol) phenyl silane | Ph Si Cl$_3$ | 211.5 | 1 |
| VIII | bis(methyl triglycol diphenyl silane | pH$_2$Si Cl$_2$ | 253 | 1 |
| IX | bis(methyl diglycol) methyl phenyl silane | Me Ph Si Cl$_2$ | 382 | 2 |
| X | bis(ethylene glycol/propylene glycol) methyl phenyl silane | Me Ph Si Cl$_2$ | 191 | 1 |
| XI | bis(tripropylene glycol) methyl phenyl silane | Me Ph Si Cl$_2$ | 95.5 | 0.5 |
| XII | triethylene glycol bis (tri propylene glycol methyl phenyl silane) | Me Ph Si Cl$_2$ | 382 | 2 |
| XIII | PEG200 bis (methyltriglycol methyl phenyl silane) | Me Ph Si Cl$_2$ | 382 | 2 |
| XIV | dipropylene glycol bis (methyl triglycol methyl phenyl silane) | Me Ph Si Cl$_2$ | 573 | 3 |
| XV | ethylene glycol bis (methyl diglycol methyl phenyl silane) | Me Ph Si Cl$_2$ | 573 | 3 |
| XVI | ethylene glycol bis (methyl monoglycol methyl phenyl silane) | Me Ph Si Cl$_2$ | 573 | 3 |
| XVII | diethylene glycol bis (ethyl triglycol methyl phenyl silane) | Me Ph Si Cl$_2$ | 382 | 2 |
| XVIII | dipropylene glycol bis (bis (methyl triglycol)phenyl silane) | Ph Si Cl$_3$ | 423 | 2 |
| XIX | diethylene glycol (bis (tri-propylene glycol mono methyl ether) phenyl silane) | Ph Si Cl$_3$ | 423 | 2 |

| Example No | Glycol Ether | Wt(g) | Mole | Pyridine Wt(g) | Pyridine Mole |
|---|---|---|---|---|---|
| II | triethylene glycol monomethyl ether | 547 | 3.3 | 261 | 3.3 |
| III | triethylene glycol monomethyl ether | 721 | 4.4 | 347 | 4.4 |
| VI | diethylene glycol monomethyl ether | 675 | 5.6 | 444 | 5.6 |
| VII | dipropylene glycol mono methyl ether | 488 | 3.3 | 261 | 3.3 |
| VIII | triethylene glycol monomethyl ether | 361 | 2.2 | 174 | 2.2 |
| IX | diethylene glycol monomethyol ether | 528 | 4.4 | 347 | 4.4 |
| X | DOW E555+ | 535 | 2.2 | 174 | 2.2 |
| XI | tripropylene glycol monomethyl ether | 247 | 1.2 | 94.8 | 1.2 |
| XII | tripropylene glycol monomethyl ethyl | 453 | 2.2 ++ | ++ | |
| XIII | triethylene glycol monomethyl ether | 361 | 2.2 | 173.8 | 2.2 |
| XIV | triethylene glycol mono methyl ether | 541 | 3.3 | 260.7 | 3.3 |
| XV | diethylene glycol monomethyl ether | 396 | 3.3 | 260.7 | 3.3 |
| XVI | ethylene glycol mono methyl ether | 251 | 3.3 | 260.7 | 3.3 |
| XVII | triethylene glycol mono ethyl ether | 392 | 2.2 | 173.8 | 2.2 |
| XVIII | triethylene glycol monomethyl ether | 722 | 4.4 | 347.6 | 4.4 |
| XIX | tripropylene glycol | 906 | 4.4 | 347.6 | 4.4 |

TABLE I-continued
mono methyl ether

| Example NO. | Glycol | Wt(g) | moles | Pyridine Wt. (g) | Pyridine mole | Toluene liters | Yield Wt(g) | Silicon % | Analysis (calc Found | Analysis calc | Chlorine zero % |
|---|---|---|---|---|---|---|---|---|---|---|---|
| II |  |  |  |  |  | 2.5 | 422 | 71 | 5.71 | 4.72 | 0.01 |
| III |  |  |  |  |  | 2.7 | 708 | 80 | 6.77 | 6.27 | 0.04 |
| VI |  |  |  |  |  | 2.5 | 610 | 78 | 6.51 | 6.06 | 0.02 |
| VII |  |  |  |  |  | 2.5 | 434 | 80 | 5.47 | 5.12 | 0.04 |
| VIII |  |  |  |  |  | 2.0 | 351 | 69 | 6.83 | 5.51 | <0.1 |
| IX |  |  |  |  |  | 2.5 | 523 | 73 | 8.36 | 7.83 | 0.04 |
| X |  |  |  |  |  | 1.5 | 547 | 91 | 4.81 | 4.64 | 0.15 |
| XI |  |  |  |  |  | 0.75 | 223 | 84 | 5.62 | 5.28 | <0.1 |
| XII | triethylene glycol | 150 | 1 | ++ | ++ | 1 | 741 | 93 | 7.61 | 7.02 | 0.023 |
| XIII | polyethylene glycol 200 | 200 | 1 | 158 | 2 | 2.5 613 | 80 | 8.84 | 7.33 | <0.1 |  |
| XIV | dipropylene glycol | 201 | 1.5 | 237 | 3 | 2.5 | 642 | 61 | 8.15 | 8.02 | <0.1 |
| XV | ethylene glycol | 93 | 1.5 | 237 | 3 | 2.5 | 518 | 64 | 12.0 | 10.4 | 1.36 |
| XVI | ethylene glycol | 93 | 1.5 | 237 | 3 | 2.5 | 412 | 61 | 12.6 | 12.4 | <0.1 |
| XVII | diethylene glycol | 106 | 1 | 158 | 2 | 2 | 614 | 88 | 8.71 | 8.02 | <0.1 |
| XVIII | dipropylene glycol | 134 | 1 | 158 | 2 | 2.5 | 791 | 80 | 6.68 | 5.63 | <0.1 |
| XIX | diethylene glycol | 106 | 1 | 158 | 2 | 2.5 | 869 | 76.6 | 7.18 | 4.94 | 0.11 |

+DOW E555 is a commercially available mono methyl ether of mixed ethylene/propylene glycol believed to have a molecular weight of about 243.
++In this reaction no pyridine was used, the H Cl being blown off with nitrogen 5 hours at the initial stage and for 36¼ hours at the second stage until no further trace of H Cl was obtained.

Each of the products were examined for their effect on the three types of rubbers most commonly used in hydraulic systems, G9 being a styrene-butadiene synthetic rubber, and is heated at 120° C. for 3 days R32 being a natural rubber and A.79 and HN89 being acrylonitrile synthetic rubbers, these latter two being heated for 3 days at 70° C. The volume increase was measured by weighing the specimen in water before and after test. The results of these tests, the viscosity at −40° C and Gilpin vapour lock tests (3mls) are given in Table 2.

TABLE 2

| Example No. | Viscosity at −40% cS | Gilpin Wet Vapour Lock ° C. | Three Day Rubber Tests G9 | Three Day Rubber Tests R32 | Three Day Rubber Tests A79 |
|---|---|---|---|---|---|
| I | 697 | 190 | 18.5 | 3.5 |  |
| II | 3506 | 254 | 7.0 | −0.02 | 23.7* |
| III | 1649 | 239 | 32.2 | 5.84 | 42.3 |
| IV | 7628 | 215 | 41.3 | 11.6 | 44.6 |
| V | 3420 | 254 | 8.3 | −0.6 | 26.9 |
| VI |  | 190 | 18.4 | 3.9 | 57.2 |
| VII | 2911 | 208 | 54.8 | 31.0 | 11.3 |
| VIII | 38000 | 144 | 20.8 | 3.6 | 38.8 |
| IX | 506 | 183 | 45.9 | 19.1 | 76.6 |
| X | 6710 | 223 | 19.7 | 2.6 | 31.4 |
| XI | 4732 |  | 76.8 | 50.6 | 12.6 |
| XII | 52876 | 220 | 34.4 | 16.8 | 7.9 |
| XIII | 35205 | 235 | 10.0 | 1.32 | 19.5 |
| XIV | 1048 | 231 | 36.1 | 8.7 | 42.7 |
| XV | 14211 | 172 | 45.8 | 25.9 | 34.3 |
| XVI | 81111 | 155 | 60.7 | 30.6 | 22.0 |
| XVII | 11333 | 202 | 39.0 | 3.9 | −4.0 |
| XVIII | 12720 | 256 | 11.4 | 1.2 | 28.2 |
| XIX | 39161 | 236 | 24.5 | 10.9 | 1.7 |
| DTD585 mineral oil | — | 100 | 136.2 | 218.3 | 2 |
| Tripropylene glycol monomethyl | — | — | 68.6 | 27.5 | 56.2 |
| Triethylene glycol monomethyl ether | — | — | 5.7 | 0.8 | 54 |

The last three members of the above Table 2 are included for comparative purposes to illustrate the relative efficacy of the aryl silanes of this invention.
*HN89 used in place of A79

In order to demonstrate the usefulness of the above compounds in a wide range of proportions in hydraulic fluids three fluids were made up as follows:

EXAMPLE A

| Product of Example VI | 90% |
|---|---|
| Triethylene glycol | 10% |

The viscosity of this fluid at −40° C was 1149 cS and the Gilpin wet vapour lock (3ml) was 196° C.

EXAMPLE B

| Product of Example X | 50% |
|---|---|
| Triethylene glycol monomethyl ether | 50% |

The viscosity of this fluid at −40° C was 1000 cS and the Gilpin wet vapour lock (3ml) was 149° C,

EXAMPLE C

| Product of Example XII | 30% |
|---|---|
| Triethylene glycol monomethyl ether | 70% |

The viscosity of this fluid was 747 cS at −40° C and the Gilpin wet vapour lock (ml) was 144° C.

All three blends also conformed to the SAEJ 1703E specification as far as water tolerance and SBR cup tests.

We claim:
1. A glycol-substituted aryl silane of the formula:

wherein (a) R is aryl;
(b) X is selected from the group consisting of

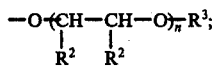
(A)

-continued $$-O-R^4-O-\underset{\underset{R'}{|}}{\overset{\overset{R'}{|}}{Si}}-R^6; \quad (B)$$

$$-O-\underset{\underset{R'}{|}}{\overset{\overset{R'}{|}}{Si}}-O-\underset{\underset{R'}{|}}{\overset{\overset{R'}{|}}{Si}}-R^6; \quad (C)$$

$$-O-\underset{\underset{R}{|}}{\overset{\overset{R'}{|}}{Si}}(CH-CH-O)_{\overline{n}}R^3; \text{ and} \quad (D)$$
$$\quad \quad \quad R^2 \ R^2$$

$$-O-\underset{\underset{R}{|}}{\overset{\overset{R}{|}}{Si}}-R^6 \quad (E)$$

in which each R is defined above, R' is as hereinafter defined, each $R^2$ is independently selected from the group consisting of hydrogen, methyl and ethyl provided that when any group $R^2$ is methyl or ethyl the group $R^2$ on the immediately adjacent carbon atom is hydrogen, $R^3$ is alkyl, $R^4$ is selected from the group consisting of diol and polyol residues, $R^6$ is selected from the group consisting of aryl and alkyl, and $n$ is an integer; and (c) each R' is, independently selected from the group consisting of groups of formula (A) as defined above, alkyl, aryl, and groups of the formula:

$$-O-R^5$$

wherein $R^5$ is alkyl and if the glycol-substituted aryl silane contains more than one group $R^5$ they may be the same or different; provided that the glycol-substituted arylsilane contains at least one group selected from the group consisting of $$-O-R^4-O- \text{ and } -O(CH-CH-O)_{\overline{n}}$$
$$\quad \quad \quad \quad \quad \quad R^2 \ R^2$$

wherein $R^2$, $R^4$ and $n$ are as defined above.

2. A glycol-substituted aryl silane as claimed in claim 1, wherein each group R is independently selected from the group consisting of phenyl and substituted phenyl groups.

3. A glycol-substituted aryl silane as claimed in claim 1, wherein each group $R^5$ is independently an alkyl group containing from 1 to 6 carbon atoms.

4. A glycol-substituted aryl silane as claimed in claim 1, wherein $n$ is from 1 to 4.

5. A glycol-substituted aryl silane as claimed in claim 1, wherein each of the groups $R^3$, $R^5$ and/or $R^6$ are alkyl groups having from 1 to 4 carbon atoms.

6. A glycol-substituted aryl silane as claimed in claim 1, wherein one or more of the groups $R^3$, $R^5$ and/or $R^6$ is an alkyl group having from 5 to 8 carbon atoms.

7. A glycol-substituted aryl silane as claimed in claim 1, wherein R is phenyl, one of the groups R' is methyl and the other of the groups R' and X are identical, both being groups of formula (A) as defined in claim 1.

8. A glycol-substituted aryl silane as claimed in claim 1 and having the formula:

$$R^3-(OCH_2-\underset{\underset{R^2}{|}}{CH})_nO-\underset{\underset{\phi}{|}}{Si}-O(-CH-\underset{\underset{R^2}{|}}{CH}-O)_{\overline{n}}-\underset{\underset{\phi}{|}}{\overset{\overset{CH_3}{|}}{Si}}-O(CH-CH_2-O)_n R^3$$
$$\quad \quad \quad \quad \quad \quad R^2 \quad \quad \quad \quad \quad \quad R^2$$

wherein $\phi$ is phenyl, $n$ is 1 to 4, and $R^2$, and $R^3$ are as defined in claim 1.

9. A glycol-substituted aryl silane as claimed in claim 1, wherein X is a group of formula (B) and each silicon atom bears at least one glycol monoether residue.

10. A glycol-substituted aryl silane as claimed in claim 1, wherein each silicon atom bears at least one glycol monoether residue which is a mixed ethylene-/propylene glycol ether residue.

11. A process for preparing a glycol-substituted aryl silane as defined in claim 1 which process comprises reacting an aryl chlorosilane of the formula:

$$A-\underset{\underset{B}{|}}{\overset{\overset{R}{|}}{Si}}-C$$

wherein R is as defined in claim 1 and at least one A, B and C is chlorine, the other two of A, B and C being the same or different and are each selected from the group consisting of chlorine, aryl, alkyl, alkoxy and groups X as defined in claim 1 with a member selected from the group consisting alkanols, diols, polyols, glycol monoethers of the formula:

$$H-O(-CH-CH-O)_{\overline{n}}R^3$$
$$\quad \quad R^2 \ R^2$$

wherein $R^2$, $R^3$ and $n$ are as defined in claim 1, or mixtures of an alkanol and said glycol monoether; provided that only one of A, B and C is a group X when X is a group selected from the group consisting of groups of Formula B, C, D or E as defined in claim 1, only one of A, B and C is chlorine and none of said groups is a group X when said reaction is with a member selected from the group consisting of diols or polyols, and only one of A, B and C is chlorine and at most one of A, B and C is alkoxy or two of A, B and C are chlorine and the third of A, B and C is not alkoxy when said reaction is with an alkanol.

12. A process as claimed in claim 11, wherein the aryl chlorosilane is reacted with a mixture of glycol monoethers.

13. A process as claimed in claim 11, wherein the aryl chlorosilane contains at least two chlorine atoms and is reacted sequentially with different glycol monoethers to obtain a glycol-substituted aryl silane having two or more glycol monoether residues.

14. A process as claimed in claim 11, wherein about 10% excess glycol monoether is employed in the or each reaction with aryl chlorosilane.

15. A process as claimed in claim 11, wherein the aryl chlorosilane contains at least two chlorine atoms and is reacted sequentially with said glycol monoether and alkanol to obtain a glycol-substituted aryl silane wherein one or more groups R' have the formula — O — R⁵ as defined in claim 1.

16. A process as claimed in claim 11, wherein the polyol is selected from the group consisting of trimethylol propane, pentaerythritol and dipentaerythritol.

17. A process for preparing a glycol-substituted aryl silane as defined in claim 1, which process comprises transesterifying a —Si—O—R group, wherein R is lower alkyl, with a member selected from the group consisting of an alcohol, a glycol, a glycol ether or a polyoxyalkylene glycol ether and in the presence of a transesterification catalyst.

18. A hydraulic fluid composition which includes as an ingredient at least one glycol-substituted aryl silane of the formula:

wherein: (a) R is aryl;
(b) X is selected from the group consisting of

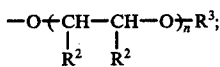 (A)

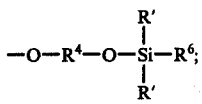 (B)

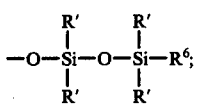 (C)

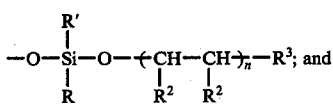 (D)

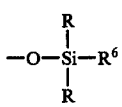 (E)

in which each R is defined above, R' is as hereinafter defined, each R² is independently selected from the group consisting of hydrogen, methyl and ethyl provided that when any group R² is methyl or ethyl the group R² on the immediately adjacent carbon is hydrogen, R³ is alkyl, R⁴ is selected from the group consisting of diol and polyol residues, R⁶ is selected from the group consisting of aryl and alkyl, and n is an integer; and (c) each R' is, independently selected from the group consisting of groups of formula (A) as defined above, alkyl, aryl, and groups of the formula:

wherein R⁵ is alkyl and if the glycol-substituted aryl silane contains more than one group R⁵ they may be the same or different; provided that the glycol-substituted arylsilane contains at least one group selected from the group consisting of

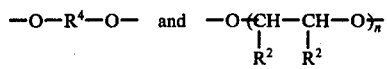

wherein R², R⁴ and n are as defined above.

19. A hydraulic fluid composition as claimed in claim 18, wherein the glycol-substituted aryl silane is used as a base stock and constitutes the major part of the composition.

20. A hydraulic fluid composition as claimed in claim 19, wherein the glycol-substituted aryl silane is present in the composition in an amount of from 75% to 99% by weight based on the total weight of the composition.

21. A hydraulic fluid composition as claimed in claim 18, wherein the glycol-substituted aryl silane is part of a blend of base stocks.

22. A hydraulic fluid composition as claimed in claim 18, wherein the glycol-substituted aryl silane is used as an additive and constitutes a minor part of the composition, the remainder of the composition being one or more base stocks.

23. A hydraulic fluid composition as claimed in claim 22, wherein the composition contains from 1% to 12% by weight of the glycol-substituted aryl silane based on the total weight of the composition.

24. A hydraulic fluid composition as claimed in claim 18, wherein the composition also includes one or more base stocks selected from the group consisting of glycol ethers, glycol esters, glycol orthoesters and borate esters.

25. A hydraulic fluid composition as claimed in claim 24, wherein the glycol ester base stock(s) is/are selected from the group consisting of those having the formulae:

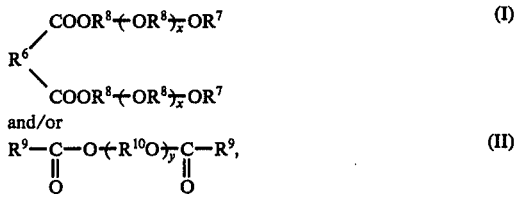

wherein R⁶ is selected from the group consisting of straight and branched chain alkylene groups containing at least 2 carbon atoms, each R⁷ is the same or different and is selected from the group consisting of alkyl radicals containing from 1 to 4 carbon atoms and phenyl, each R⁸ is the same or different and is selected from the group consisting of ethylene, propylene and butylene groups, each x is the same or different and is 0 or an integer of from 1 to 3, each R⁹ is the same or different and is selected from the group consisting of ethyl and methyl, each R¹⁰ is the same or different and is selected from the group consisting of ethylene and propylene groups and y is an integer.

26. A hydraulic fluid composition as claimed in claim 24, wherein the borate ester base stock(s) is/are selected from the group consisting of those have the formulae:

 (III)

-continued

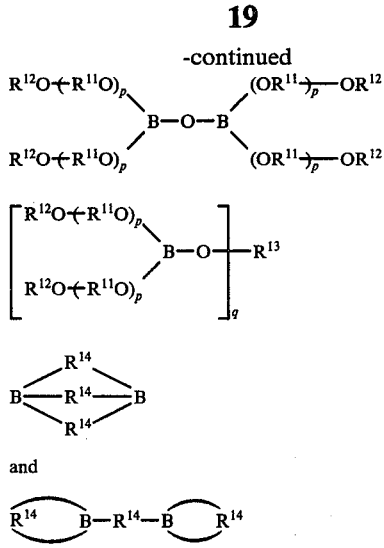

and (VII)

wherein each $R^{11}$ is the same or different and is selected from the group consisting of straight and branched chain alkyl groups, each $R^{12}$ is the same or different and is an alkyl group, each $p$ is the same or different and is an integer, $q$ is an integer of from 2 to 6, $R^{13}$ is the residue of a member selected from the group consisting of di- or poly-hydroxy organic compounds having a number of reactive hydroxy groups equal to $q$, and each $R^{14}$ is the same or different and is the residue of a di-hydroxy organic compound which residue is attached to each boron atom via an oxygen atom.

27. A hydraulic fluid composition as claimed in claim 24, wherein the glycol orthoester base stock(s) is/are selected from the group consisting of those having the formulae:

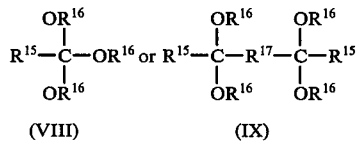

(VIII)    (IX)

wherein $R^{15}$ is selected from the group consisting of a hydrogen atom, an alkyl radical containing from 1 to 5 carbon atoms, and the same as $OR^{16}$; each $R^{16}$ is the same or different and each is selected from the group consisting of an alkyl radical containing from 1 to 4 carbon atoms, an oxyalkylene glycol monoether radical, and a polyoxyalkylene glycol monoether radical containing from 2 to 20 alkylene oxy units, provided that at least one $R^{16}$ is selected from the group consisting of an oxyalkylene glycol monoether radical and a polyoxyalkylene glycol monoether radical; and $R^{17}$ is an alkylene radical containing from 1 to 12 carbon atoms, provided that $R^{15}$ is then the same as $OR^{16}$ or $R^{17}$ is the group $-O\text{-}(R^{18}O)_z$, wherein each $R^{18}$ is the same or different and each is an alkylene radical containing from 2 to 8 carbon atoms and $z$ is an integer from 1 to 6.

28. A hydraulic fluid composition as claimed in claim 24, wherein the composition contains a mixture of glycol ether base stock and borate ester base stock of formula (III) as defined in claim 26.

29. A hydraulic fluid composition as claimed in claim 24, wherein the composition contains a mixture of one or more glycol ester base stocks selected from the group consisting of those of formula (I) and/or (II) as defined in claim 25 with one or more borate ester base stocks selected from the group consisting of those of formulae (III) to (VII) as defined in claim 26.

30. A hydraulic fluid composition as claimed in claim 18, wherein the composition also comprises a lubricity additive.

31. A hydraulic fluid composition as claimed in claim 18, wherein the composition also comprises a corrosion inhibitor.

32. A hydraulic fluid composition as claimed in claim 18, wherein the composition also comprises an antioxidant.

33. A hydraulic fluid composition as claimed in claim 18, wherein the composition also comprises a polyoxyalkylene glycol and/or an ether or ester thereof.

34. A hydraulic fluid composition as claimed in claim 18, which composition has a kinematic viscosity at $-40°$ C of not more than 5000 cst and a boiling point of at least 260° C.

35. A process as claimed in claim 11 wherein hydrogen chloride liberated in the process is removed with an acid acceptor or inert gas purge.

36. A hydraulic fluid composition as claimed in claim 18 wherein in the glycol-substituted aryl silane each group R is independently selected from the group consisting of phenyl and substituted phenyl groups.

37. A hydraulic fluid composition as claimed in claim 18 wherein in the glycol-substituted aryl silane each group $R^5$ is independently an alkyl group containing from 1 to 6 carbon atoms.

38. A hydraulic fluid composition as claimed in claim 18 wherein in the glycol-substituted aryl silane $n$ is from 1 to 4.

39. A hydraulic fluid composition as claimed in claim 18 wherein in the glycol-substituted aryl silane each of the groups $R^3$, $R^5$ and/or $R^6$ are alkyl groups having from 1 to 4 carbon atoms.

40. A hydraulic fluid composition as claimed in claim 18 wherein in the glycol-substituted aryl silane one or more of the groups $R^3$, $R^5$ and/or $R^6$ is an alkyl group having from 5 to 8 carbon atoms.

41. A hydraulic fluid composition as claimed in claim 18 wherein in the glycol-substituted aryl silane R is phenyl, one of the groups R' is methyl and the other of the groups R' and X are identical, both being groups of formula (A) as defined in claim 18.

42. A hydraulic fluid composition as claimed in claim 18 wherein the glycol-substituted aryl silane has the formula:

$$R^3-(OCH_2-CH)_nO-\underset{\underset{\phi}{|}}{\overset{\overset{CH_3}{|}}{Si}}-O-(CH-CH-O)_n-\underset{\underset{\phi}{|}}{\overset{\overset{CH_3}{|}}{Si}}-O(CH-CH_2-O)_n R^3$$
$$\phantom{R^3-(OCH_2-CH)_nO-Si-O-}R^2\phantom{-Si-O-}R^2\ R^2\phantom{-Si-O(CH-CH_2-O)_n}R^2$$

wherein $\phi$ is phenyl, $n$ is 1 to 4, and $R^2$, and $R^3$ are as defined in claim 18.

43. A hydraulic fluid composition as claimed in claim 18 wherein in the glycol-substituted aryl silane X is a group of formula (B) and each silicon atom bears at least one glycol monoether residue.

44. A hydraulic fluid composition as claimed in claim 18 wherein in the glycol-substituted aryl silane each silicon atom bears at least one glycol monoether residue which is a mixed ethylene/propylene glycol ether residue.

* * * * *